United States Patent
Jaros et al.

(10) Patent No.: US 9,131,996 B2
(45) Date of Patent: Sep. 15, 2015

(54) DENTAL SCALER

(71) Applicant: Coltene Whaledent, Inc., Cuyahoga Falls, OH (US)

(72) Inventors: Jeff Jaros, Cuyahoga Falls, OH (US); Randy Weakland, Cuyahoga Falls, OH (US)

(73) Assignee: Coltene Whaledent, Inc., Cuyahoga Falls, OH (US)

( * ) Notice: Subject to any disclaimer, the term of this patent is extended or adjusted under 35 U.S.C. 154(b) by 486 days.

(21) Appl. No.: 13/675,381

(22) Filed: Nov. 13, 2012

(65) Prior Publication Data
US 2013/0122459 A1    May 16, 2013

Related U.S. Application Data

(60) Provisional application No. 61/559,500, filed on Nov. 14, 2011.

(51) Int. Cl.
*A61C 17/20* (2006.01)
*A61C 3/03* (2006.01)
*A61C 1/00* (2006.01)
*A61C 1/07* (2006.01)

(52) U.S. Cl.
CPC ............. *A61C 17/20* (2013.01); *A61C 1/0015* (2013.01); *A61C 3/03* (2013.01); *A61C 1/07* (2013.01)

(58) Field of Classification Search
CPC ......... A61C 17/20; A61C 3/03; A61C 1/0015
See application file for complete search history.

(56) References Cited

U.S. PATENT DOCUMENTS

| | | | | |
|---|---|---|---|---|
| 4,984,449 A | * | 1/1991 | Caldwell et al. | 73/49.2 |
| 5,151,085 A | * | 9/1992 | Sakurai et al. | 604/22 |
| 5,180,363 A | * | 1/1993 | Idemoto et al. | 604/22 |
| 5,451,161 A | * | 9/1995 | Sharp | 433/119 |
| 5,730,594 A | * | 3/1998 | Sharp | 433/119 |
| 2003/0222535 A1 | * | 12/2003 | Gofman et al. | 310/316.01 |

* cited by examiner

*Primary Examiner* — Zeev V Kitov
(74) *Attorney, Agent, or Firm* — Vorys, Sater, Seymour and Pease LLP

(57) ABSTRACT

A dental scaler apparatus includes a low power transformer that is tuned to the operating frequency of a detachable scaler insert connected to the handle of the scaler apparatus by selectively connecting corresponding banks of parallel adjustment capacitors by engaging corresponding switches coupled to each of the adjustment capacitors.

6 Claims, 2 Drawing Sheets

DENTAL SCALER

CROSS-REFERENCE TO RELATED APPLICATIONS

The present application claims priority from U.S. Provisional Patent Application No. 61/559,500 filed on Nov. 14, 2011, the contents of which are hereby wholly incorporated by reference.

FIELD OF THE INVENTION

The present invention relates generally to a circuit for driving an ultrasonic scaling probe suitable for use in dentistry, and more specifically, to a circuit that is stable, has fine tuning and auto-shutdown mechanisms.

BACKGROUND OF THE INVENTION

Conventional dental scalers include an energizing coil enclosed within a handle where an oscillator of a drive circuit is coupled to the coil for applying an oscillatory current to the coil. Two standard magnetostrictive scaler tool sets are typically used in the dental business, one is 25 kHz and the second is 30 kHz.

SUMMARY OF THE INVENTION

The present invention is directed to an objective of providing stable operation of a dental scaler apparatus while lowering the power range of the apparatus in order to reduce possible dental damage caused by the use of such an apparatus. In view of this objective, the present invention is directed to a novel tuning mechanism for fine tuning the operating frequency of a low power dental scaler.

DETAILED DESCRIPTION OF THE INVENTION

Figure 1:
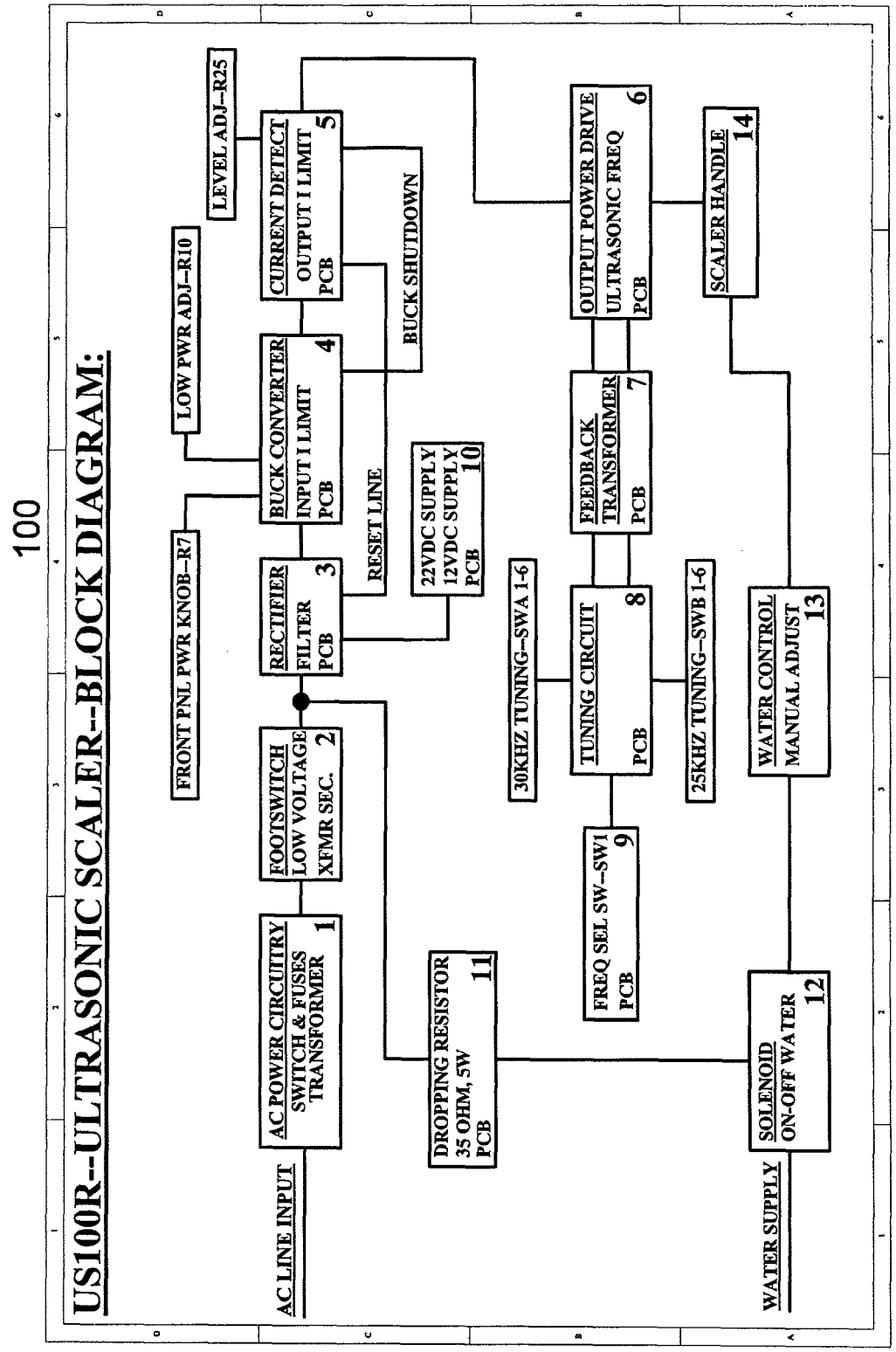
FIG. 1 is a block diagram illustrating a dental scaler apparatus according to the present invention.

In order to oscillate the scaler handle, different drive circuits can be used that utilize: 1) microprocessor 2) Phase Locked Loop (PLL) 3) LC oscillator topology. It is desirable to use an LC drive for its simple design while meeting operational goals. Tuning is straight forward and incorporates the feedback transformer inductance (L) and a switchable capacitor bank (C), specifically arranged in a binary fashion, with enough bits (binary cap arrangement) to provide a smooth range of adjustment for C. The transformer is the handle feedback mechanism for the tuning arrangement.

For such an LC resonant circuit tuning follows the standard resonant formula of $F=1/\{2*pi*(LC)**0.5\}$. Specific use of the air-core feedback transformer with its secondary tuning "L" enables a temperature stable design and tight tolerance winding (and tight tolerance L). Specific use of capacitors of a tight tolerance enables a tight C with respect to value and temperature. Overall stable tuning is enabled by the unique combination of the air-core transformer, tight tolerance capacitors, and the binary capacitor arrangement—thus enabling a practical tuning mechanism for manufacturing.

By utilizing two sets of binary arranged capacitors the design can accommodate both 25 KHZ and 30 KHZ operation. The two sets of capacitors are switched by a simple relay, controlled by a slide switch. This allows use of 25 KHZ and 30 KHZ magnetostrictive insert tools. Tuning design variances can be accommodated through turns ratio changes, added resistance, and supply voltage to attain lower and higher circuit Q's.

In order to attain lower power, a greater feedback signal was necessary and this was accomplished by increasing the turns ratio from 85/9 (20 W to 40 W range) to 208/9 (~7 W to ~25 W range), thus supplying adequate feedback at low output levels.

The small transformer secondary L tolerance (and temperature independence—part of resonant electronics tuning) in conjunction with close tolerance capacitors (also low variation with temperature) allow tuning that is fine enough and stable with temperature, the combination being a specific design approach to allow this circuit topology to be implemented. The bank of tuning capacitors, specifically arranged in a binary fashion, with an adequate number of steps is the capacitive equivalent of a resistive potentiometer—allowing fine capacitive adjustment in tuning—this arrangement also enables the use of higher capacitive values needed to enable tuning with the inductance (L) in the circuit. This is a specific arrangement that allows smooth adjustment, tight tolerance, and cannot be done using a single variable capacitor (or a small number in a non-binary arrangement)—as they are not available in such high values (and physically small). The number of binary steps can be altered depending upon the fineness of the tuning desired. Also, capacitor tolerances can be increased or decreased as needed. The result is an LC tuning that can be made practical (would not otherwise be) for our given application (and has not been attempted via other dental scalers).

FIG. 1 illustrates an exemplary embodiment of an ultrasonic dental scaler 100 according to the present invention. As shown in FIG. 1, the dental scaler 100 may be powered by a standard AC power source with AC power circuitry 1 connected to a footswitch 2, which is, in turn, connected to a rectifier 3 for providing DC power to the scaler 100. An operator may operate the footswitch 2 to connect the AC power circuitry 1 to the rectifier 3 and, thus, power to the scaler 100.

The rectifier 3 is connected to a buck converter 4 that converts the input DC voltage from the rectifier 3 to a desirable output voltage through a current detector 5 to an output power drive 6. The current detector 5, which will be described in further detail, detects the output of the buck converter 4 to limit its current output. When a current from the buck converter 4 exceeds a limit, a buck shutdown from the current detector 5 is triggered to shutdown the buck converter 4.

The output of the buck converter 4 that does not exceed the current limit is passed through to the output power drive 6, which drives the scaler handle 14. The operating frequency of the output power drive 6 is controlled by a tuning circuit 8 via a feedback transformer 7. A frequency selection switch 9 is operable to select an operating frequency of the tuning circuit 8 for output via the feedback transformer 7 to the output power drive 6 to drive the scaler handle 14 at the operating frequency. Exemplary standard operating frequencies for a dental scaler are 25 kHz and 30 kHz. Accordingly, a 25 kHz bank of Tuning Adjustment Capacitors and Switches and a 30 kHz bank of Tuning Adjustment Capacitors and Switches are connected to the tuning circuit 8 for precision tuning at the respective operating frequencies.

Separately, the scaler handle 14 is supplied with water using a solenoid 12 that is controlled by the footswitch 2 via a dropping resistor 11, whereby the solenoid 12 is turned on and off by operating the footswitch 2. Water is supplied by the solenoid 12, when turned on, via a manually adjustable water control 13 to the scaler handle 14.

Figure 2:
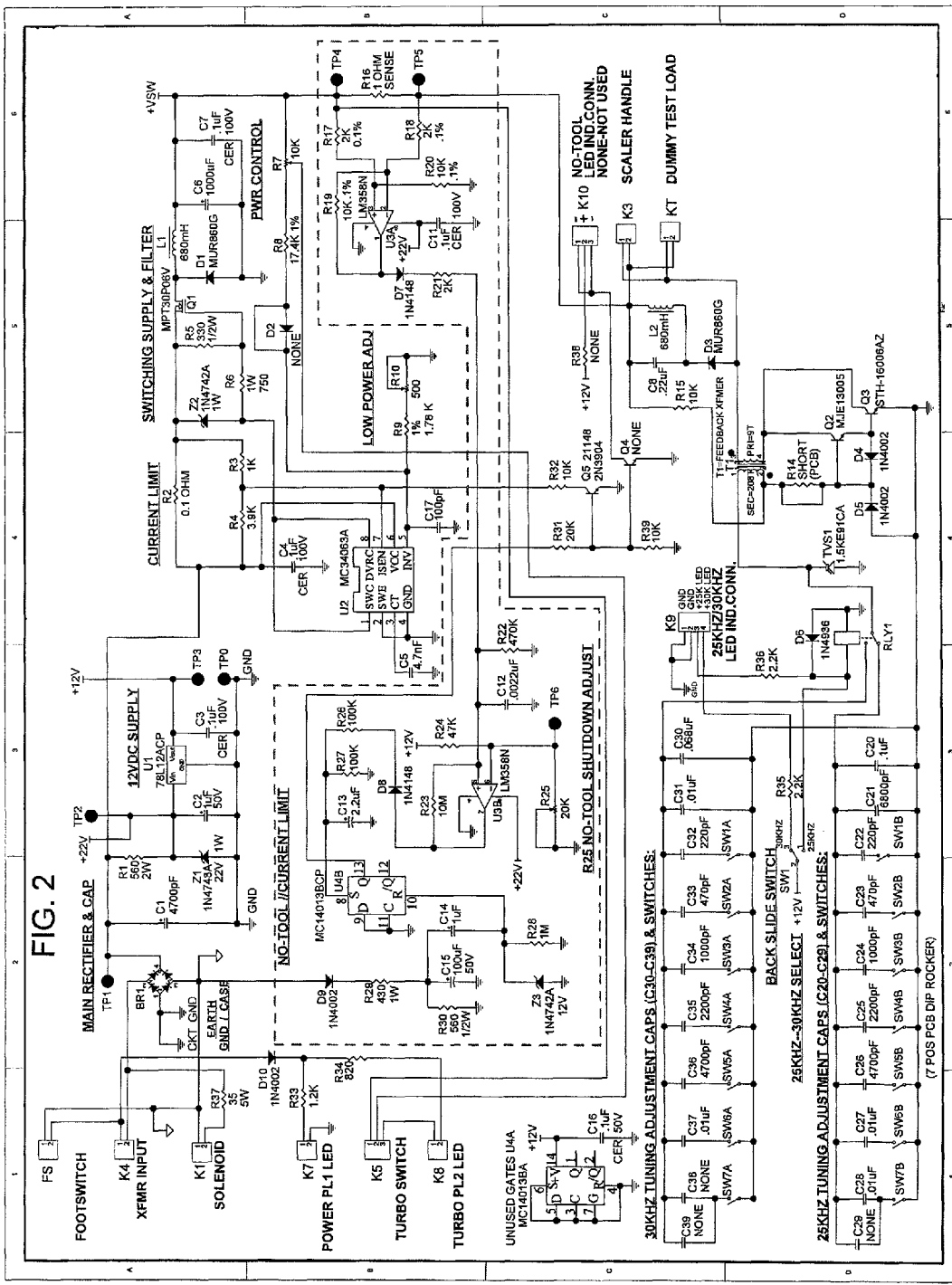
FIG. 2 is a circuit diagram detailing an exemplary embodiment of the dental scaler apparatus according to the present invention.

FIG. 2 illustrates another exemplary embodiment of the dental scaler according to the present invention in correspondence with the exemplary embodiment illustrated in FIG. 1. As shown in FIG. 2, a footswitch 2 is connected and controls a transformer input (K4), which is an input from a 28 VAC secondary power transformer that may be comprised in a circuit corresponding to the AC power circuitry 1 illustrated in FIG. 1. Footswitch 2 also connects to solenoid (K1) corresponding to solenoid 12 illustrated in FIG. 1 via a resistor (R37) corresponding to dropping resistor 11 illustrated in FIG. 1.

A main rectifier may comprise a diode bridge (BR1) and capacitor (C1), and it is supplied with a 12 VDC and 22 VDC supply that may comprise a regulator (U1), resistor (R1), zener diode (Z1), and capacitors (C2) (C3). The 22V supply can be adjusted so that it is higher than the buck output voltage to provide proper op-amp operation.

A buck converter may comprise a current limit having resistors (R2), (R3), and (R4), a regulator (U2), and a switching supply comprising a zener diode (Z2), diode (D1), transistor (Q1), inductor (L1), capacitors (C6) (C7), and a resistor (R5).

A front panel power knob for controlling the buck converter may be implemented with a diode (D2), resistor (R8), variable resistor (R7), and a turbo switch (K5). The front panel may also include a LED (K8) for indicating a status of the turbo switch. The buck converter may also be controlled with a lower power adjuster comprising a resistor (R9) and an variable resistor (R10).

A sensing resistor (R16) may be used for a current detect, which may be implemented with a differential amplifier (U3A), resistors (R17)-(R21), capacitor (C11), diode (D7). The detected current may be used for a "no-tool" current limit, which may be implemented using a flip flop (U4B), comparator/amplifier (U3B), capacitors (C12)-(C15), resistors (R22)-(R24), (R26)-(R30), diode (D8), and zener diode (Z3). And the threshold current level may be adjusted using a variable resistor (R25). A reset line to the main rectifier may be implemented using an amplifier (Q5) and resistors (R31)-(R32). And a "no-tool" LED (K10) may be driven using an amplifier (Q4) and resistor (R39).

The buck converter and current detect circuitry cooperate to form a shutdown circuit that stops the scaler from outputting power when there is no tool inserted in the driver handle. The high line sense resistor (R16) and differential amplifier (U3A), then feeds a comparator (U3B), which is used to adjust current sense level, that sets flip-flop (U4B), which in turn drives a transistor to shutdown the switching power supply. To re-start the power, the foot switch may be released and depressed again, which in turn re-sets the flip-flop (U4B) and allows power again.

A frequency selection switch (SW1) switches between 25 kHz and 30 kHz operating frequencies. For each operating frequency, a bank of capacitors and switches are connected in parallel for fine tuning the scaler to the operating frequency. The switch (SW1) connects to capacitors (C20)-(C28) and switches (SW1B)-(SW7B) for 25 kHz. An extra place (C29) may be included for adding an optional capacitor. The scaler may be fine tuned to 25 kHz by opening/closing the respective switches (SW1B)-(SW7B). The switch (SW1) connects to capacitors (C30)-(C37) and switches (SW1A)-(SW7A) for 30 kHz via a resistor (R35). Extra places (C38) and (C39) may be included for adding optional capacitors. The scaler may be fine tuned to 30 kHz by opening/closing the respective switches (SW1A)-(SW7A).

In traditional engineering practice a fixed capacitor and a variable inductor are used to tune circuits, since a wide range of tunable inductors exists and very little exists for tunable capacitors in the range of our scaler need (very large values). Disadvantageously, such a variable inductor would be exposed to high enough temperature swings as to de-tune the inductor, an inherent flaw of using a variable inductor. Thus, for stable scaler tuning with respect to temperature an air-cored inductor with a low temperature coefficient (or drift) is used. Since such an inductor suffers from a low tolerance for variable operating parameters for a desired output frequency, an effective means for fine tuning the parameters of the overall circuitry is needed to operate the scaler at the respective 25 kHz and 30 kHz frequencies.

Thus, banks of capacitors having the same or variable tolerances—for example, 2.5%-10%—may be selectively switched on, in binary fashion (very effective large cap value capacitive trimpot—equivalent to resistive trimpot), to fine tune the operating frequency of the scaler. The 25 kHz bank comprises fixed capacitors C20 and C21, with capacitances of 0.1 µF and 6800 pF, respectively, connected in parallel. Thus, the core operating capacitance is about 0.1068 µF. For adjustment capacitors C22-C28, C22 is 220 pF and C23 is 470 pF. Either value can be selected. However, if both are selected (by switches SW1B and SW2B) then the value 690 pF can be obtained. With 7 active switches 128 combinations—different capacitors—can be obtained for tuning purposes. If 6 capacitors are used, then 64 different capacitances can be obtained. Even though switched capacitors are used on occasion, they are of limited value for our application unless the binary arrangement is used and enough caps used to provide a smooth tuning range—and used in conjunction with a tight tolerance transformer, of which an air-core type is used. The combination is very effective.

The invention claimed is:

1. A dental scaler apparatus, comprising,
 a handle configured to connect and drive power to a detachable scaler tool insert;
 an air-core feedback transformer connected to the handle for providing analog feedback from the detachable scaler tool insert; and
 a tuning circuit connected to the air-core feedback transformer for matching an operating frequency of the detachable scaler tool insert, said tuning circuit comprising:
 a plurality of first tight tolerance capacitors connected in parallel, the first tight tolerance capacitors each being coupled to corresponding first binary switches that are selectively engaged to adjust a first capacitance of said plurality of first tight tolerance capacitors;
 a plurality of second tight tolerance capacitors connected in parallel, the second tight tolerance capacitors each being coupled to corresponding second binary switches that are selectively engaged to adjust a second capacitance of said plurality of second tight tolerance capacitors; and
 a selection switch for switching between the plurality of first tight tolerance capacitors and the plurality of second tight tolerance capacitors to match the operating frequency,
 wherein the first capacitance and the second capacitance are adjusted to match respective operating frequencies of different types of scaler tool inserts.

2. The dental scaler apparatus of claim 1, wherein the air-core feedback transformer has a feedback ratio of approximately 208/9.

3. The dental scaler apparatus of claim 1, wherein the first capacitance is adjusted to match an operating frequency of approximately 25 kHz and the second capacitance is adjusted to match an operating frequency of approximately 30 kHz.

4. The dental scaler apparatus of claim 1, wherein each of the first tight tolerance capacitors have different capacitances from one another and each of the second tight tolerance capacitors have different capacitances from one another.

5. The dental scaler apparatus of claim 1, wherein the first tight tolerance capacitors are connected in parallel to two parallel fixed capacitors with capacitances of approximately 0.1 μF and 6800 pF, respectively, and the second tight tolerance capacitors are connected in parallel to two parallel fixed capacitors with capacitances of approximately 0.01 μF and 0.068 μF, respectively.

6. The dental scaler apparatus of claim 1, wherein the first tight tolerance capacitors and the second tight tolerance capacitors comprise capacitors with capacitances of approximately 0.01 F, 4700 pF, 2200 pF, 1000 pF, 470 pF, and 220 pF connected in parallel.

\* \* \* \* \*